United States Patent [19]

Giele et al.

[11] Patent Number: 5,531,783
[45] Date of Patent: Jul. 2, 1996

[54] PACING LEAD WITH X-RAY VISIBLE SOLUBLE COVERING AND METHOD OF INSERTING SAME INTO A PATIENT'S HEART

[75] Inventors: Vincent Giele, Dieren, Netherlands; Marc Berkhof, Kapellen, Belgium

[73] Assignee: Vitatron Medical, B.V., Dieren, Netherlands

[21] Appl. No.: 372,971

[22] Filed: Jan. 17, 1995

[51] Int. Cl.$^6$ ............................................. A61N 1/05
[52] U.S. Cl. ........................... 607/126; 128/642; 607/127
[58] Field of Search ............................. 607/116, 120, 607/122, 126, 127, 128, 130, 131; 128/642

[56] References Cited

U.S. PATENT DOCUMENTS

| | | | |
|---|---|---|---|
| 3,736,939 | 6/1973 | Taylor | 604/265 |
| 4,827,940 | 5/1989 | Mayer et al. | 128/642 |
| 4,876,109 | 10/1989 | Mayer et al. | 427/2 |
| 4,919,891 | 4/1990 | Yafuso et al. | 128/642 X |
| 5,003,990 | 4/1991 | Osypka | 607/127 X |
| 5,261,417 | 11/1993 | Osypka | 607/127 |
| 5,374,287 | 12/1994 | Rubin | 607/131 |

*Primary Examiner*—William E. Kamm
*Assistant Examiner*—Jeffrey R. Jastrzab
*Attorney, Agent, or Firm*—Woodcock Washburn Kurtz Mackiewicz & Norris

[57] ABSTRACT

A body implantable lead is provided, suitably a pacing lead for delivering pacing stimulus pulses to a patient, the lead having a fixation element such as a helix at its distal tip. The lead is provided with a soluble covering over the helix, which covering presents a smooth surface during insertion of the lead transvenously and dissolves away after a predetermined time in the patient's body, thereby exposing the anchor element. The lead is further improved by combining a radiopaque or angiographic contrast material with the protective coating, so that the physician carrying out the implantation procedure can monitor and see exactly when the coating has dissolved, whereupon the fixation element can be directly attached to the patient's heart wall.

12 Claims, 1 Drawing Sheet

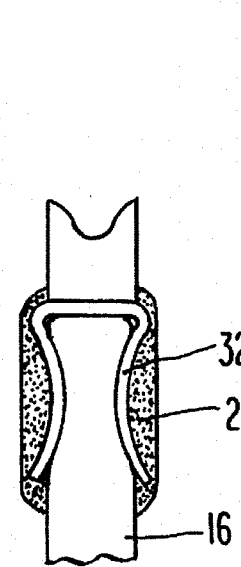
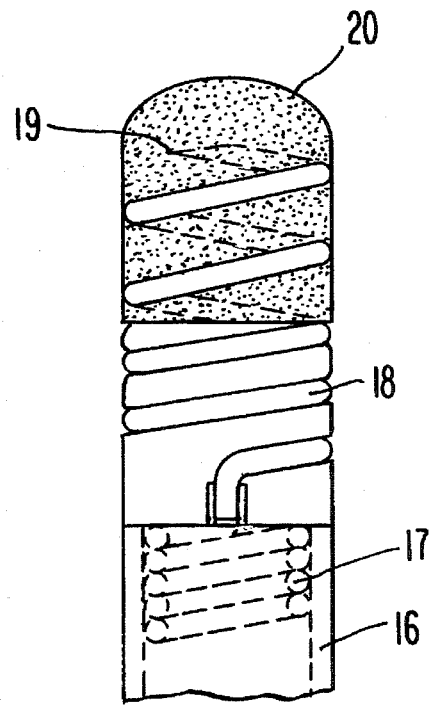
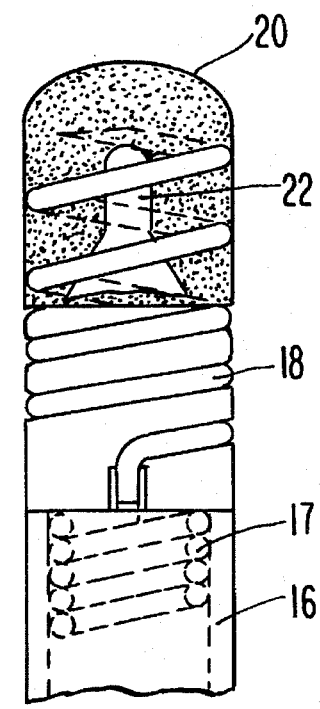
*Fig.1C*  *Fig.1A*  *Fig.1B*
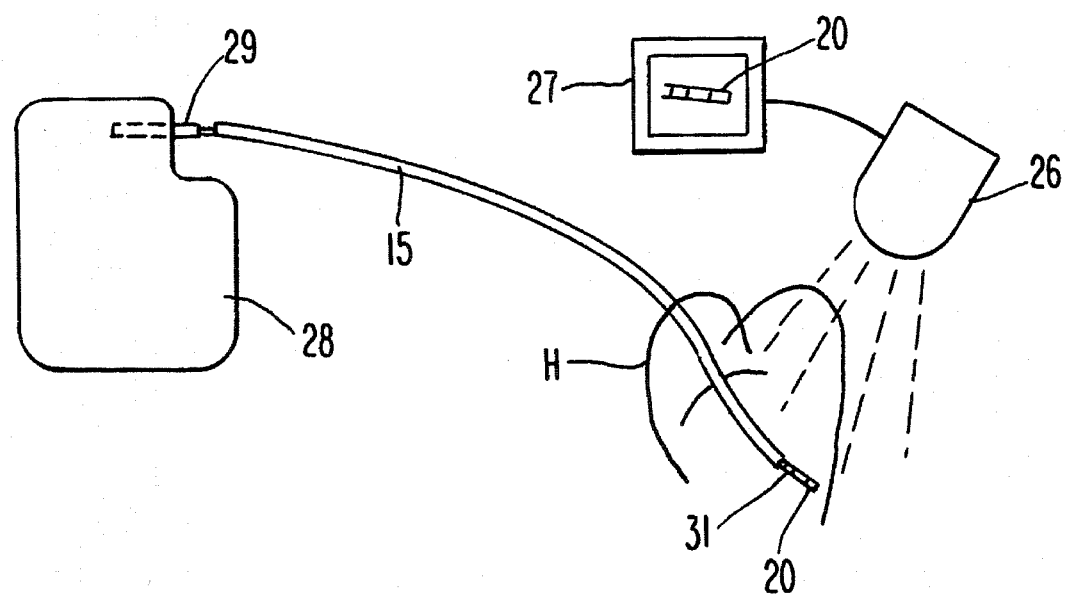
*Fig.2*

PACING LEAD WITH X-RAY VISIBLE SOLUBLE COVERING AND METHOD OF INSERTING SAME INTO A PATIENT'S HEART

BACKGROUND OF THE INVENTION

1. Field of the Invention

This invention relates to body implantable leads and, in particular, pacing leads having a distal fixation element for attachment to the inner wall of a patient's heart.

2. Description of the Prior Art

The efficacy of cardiac pacing has been widely accepted for some time now. As is well known, a pacing system comprises the basic combination of a generator, or pacemaker, and a lead. The pacemaker performs the basic function of generating pacing pulses, and also receives sensed heartbeat signals and other sensor signals for determining when pacing pulses are to be delivered and at what rate. The pacemaker is operatively connected to the heart tissue by the lead, which carries the generated pacing pulses to the heart and carries sensed heart signals from the heart back to the pacemaker. The pacing lead is fixed to the pacemaker at the proximal end by known techniques, and the distal end must be positioned at a desired location adjacent to heart wall in order to secure optimized chronic performance. In order to secure the distal end of the lead to the heart wall, many leads employ an anchoring dement such as a helical coil, barbs or the like. A great many different anchoring elements are known in the art and are disclosed in the patent literature. For the purposes of this invention, the helix, or screw-in element, will be used as illustrative, it being understood that the invention is not limited and is applicable to other types of anchoring elements.

In practice, the physician must introduce the lead intravenously into the heart, position the distal tip adjacent the heart wall so that an optimum threshold is obtained and then, in the case of a lead with an active anchor element, secure the element into the heart wall. The intravenous introduction of the lead requires that the lead be flexible and small in diameter, and devoid of any protruding element or part which would obstruct passage through the vein. Thus, the presence of a distal anchor element can carry the substantial disadvantage of making the intravenous insertion much more difficult. In order to overcome the disadvantage posed by the anchor element to the insertion process, a number of lead designs have been proposed and implemented, with varying degrees of success. Recently, there has been disclosed a cardiac pacing electrode having a soluble coveting which surrounds the fixation helix which is mounted at the distal tip end. Such a coveting has size, shape and solubility characteristics such that it maintains its smooth outer form during the transvenous insertion process, but thereafter dissolves so as to expose the anchor helix or other like anchor element. Reference is made to U.S. Pat. Nos. 4,827,940 and 4,876,109, which disclose such a soluble covering for a cardiac pacing electrode.

The problem that remains with the covering as described in the aforementioned two patents, is that the implantation procedure is necessarily interrupted while the physician waits a sufficient time to permit full dissolution of the soluble coveting. In practice, the physician, or physician's assistant, has to either wait a specified time or make measurements such as impedance drop, before screwing the lead into the heart tissue. For an experienced and adept implanter, this introduces an annoying delay, since invariably it is necessary to overwait in order to ensure that the soluble coating has indeed dissolved. What is thus desired in the art is a lead with means for providing an instant indication as to when the coating has dissolved, so that the fixation element can be fixed to the heart wall without delay.

SUMMARY OF THE INVENTION

It is an object of this invention to provide an implantable lead, and in particular an implantable pacing lead which carries an active fixation element at its distal end, the lead having a coating or covering over the fixation element, the coating having characteristics to provide that it dissolves within a reasonable time upon insertion into the patient's heart. The lead further has means for providing a real time indication to the attending physician of when the coating has dissolved, so that the physician can proceed directly to fix the distal fixation dement to the patient's heart wall, as soon as possible and with minimum delay.

In accordance with the above object, there is provided an implantable lead having distal and proximal ends and a flexible length between such ends, the lead having a fixation dement at its distal end for effecting fixation of the lead to the inside of the heart wall, the lead having a covering over at least a portion of the fixation dement to provide a smooth outer surface so as to facilitate insertion of the lead transvenously into the heart. The covering is soluble in body fluids and has dissolving or dissolution characteristics selected so that it dissolves only after being in the body fluids for at least a predetermined time. The covering is improved by having a radiopaque or like material within at least a portion thereof to render it x-ray visible until it dissolves, whereby the lead tip can be monitored to determine first when the fixation element is proximate to the heart tissue, and particularly when the covering has dissolved.

In the practice of this invention, using a pacing lead, the physician inserts the lead transvenously to the point where the distal tip is in the patient's heart. The physician monitors the radiopaque material, and upon seeing that the material has dissolved, proceeds directly to attach the distal tip to the heart wall.

BRIEF DESCRIPTION OF THE DRAWINGS

FIG. 1A is a diagrammatic representation of the distal tip end of a lead in accordance with this invention;

FIG. 1B is a diagrammatic representation of the distal tip end of an alternate embodiment, providing a coating capsule with a cavity for retaining radiopaque material.

FIG. 1C is a representation of a lead where the coating covers tines in a folded position until it dissolves.

FIG. 2 is a system block diagram illustrating the lead of this invention in combination with a pacemaker and x-ray equipment.

DESCRIPTION OF THE PREFERRED EMBODIMENTS

Referring now to FIG. 1A, there is shown a representation of the distal end portion of a lead in accordance with this invention. The lead has a casing 16, running substantially the length of the lead from the proximal to the distal end, and a coiled conductor 17 which provides transmission of electrical signals from the proximal to distal end, and vice versa. Coil 17 is connected mechanically and electrically at the distal tip end to a helical fixation element 18, as illustrated. Helix 18 may be, as illustrated here, a distal electrode as well as a fixation element. Alternately, as is well known, a separate distal electrode or pair of electrodes may be provided at the distal tip. Such a separate distal electrode 31 (see FIG. 2) is preferably a small micro electrode of 1.5–3.0 mm² surface area, and is steroid eluting.

As illustrated in FIG. 1A, the helix 18 has a terminating end 19 which has an appropriately sharp tip so as to aid screwing of the helix into the heart wall. The portion of helix 18 which is to be free for screwing into the heart wall is embedded in and covered by a covering 20, as illustrated, which is shaped so as to provide smooth passage of the distal end of the lead through the patient's veins. In a first embodiment, the coveting is made of mannitol, or a like material which has desired dissolution characteristics. These characteristics are such that it dissolves when placed in body fluids, i.e. blood, within a predetermined time, e.g., about 3–4 minutes. The mannitol or like material must, of course, be non-toxic and biocompatible in all respects. Further, its melting point must be sufficiently high so that it maintains its structural integrity, and thus its outer shape, until it dissolves within the heart. All of these requirements are collectively herein referred to as the characteristics of the coating. It is understood that other like materials in addition to mannitol can be employed in the practice of this invention.

Further in accordance with this invention, the coveting is mixed with a radiopaque material, or angiographic contrast material. Such radiopaque material is carried with the distal tip as it is inserted into position within the heart, and is x-ray visible until the covering is dissolved. By constantly monitoring the distal tip as it is positioned within the heart, the physician doing the procedure can know instantly when the helix is free for insertion into the heart wall, and proceed directly to take the step of screwing it into the heart wall.

Although FIG. 1A illustrates the entire covering 20 as being in the form of a capsule, and with the mannitol uniformly mixed with the radiopaque material, it is to be noted that any portion of the coating can be so mixed or impregnated with the radiopaque or angiographic contrast material. Thus, the capsule or coating 20 may have only an exterior coating of angiographic contrast material, or any other portion can be immpregnated so long as it is sufficient to provide a good image.

Referring to FIG. 1B, there is shown an alternate embodiment wherein the coating 20 is provided with an inner cavity 22, which cavity is filled with angiographic contrast material. The soluble element 20 can be formed by any suitable process, including molding.

In another embodiment as shown in FIG. 1C, the fixation element may be tines, as are conventionally used in pacing leads, and the covering covers the tines 32 so as to hold them folded against the lead casing until the covering dissolves.

The following is an illustrative example of a method of preparing the distal tip end of a lead so as to provide a suitable coating which protects and shields the anchor element, wherein the coating is suitably soluble and provides the desired angiographic contrast: The mannitol is melted and mixed with x-ray visible material so that it is caramelized, like sugar. The melted substance is then molded or casted around the helix. As the temperature of the substance lowers, it hardens and fixes on the helix.

Referring now to FIG. 2, there is shown a schematic representation of a pacing and monitoring system in accordance with this invention. The lead 15 is illustrated having a proximal end pin 29 which is inserted into and mechanically and electrically connected to pacemaker 28. Coil conductor 17 is electrically connected to pin 29, so as to provide electrical connection between the pacemaker and the distal end of the lead. The lead 15 is inserted, as discussed above, into the heart H, so that the coating 20 is positioned at a desirable location adjacent to heart wall. There is illustrated an electrode 31 which, as discussed above, may be the helical element or may be a separate element mounted at the distal tip. Also shown is x-ray monitoring device 26, interconnected with a monitor 27. By watching the image on monitor 27, the physician can determine when the coating 20 has dissolved, such that fixation can be accomplished. It is to be noted that the procedure has the further advantage of permitting the physician to monitor the path of the distal tip as it is inserted into the heart, thereby aiding the positioning of the distal tip at a desired location adjacent the heart wall.

What is claimed is:

1. An implantable lead having a distal end and an electrode near said distal end, a proximal end, a flexible length between said distal and proximal ends, and a conductor connecting said proximal end and said electrode, said lead having a fixation element at about said distal end for effecting fixation to body tissue at a selected location in a patient, and a covering over at least a portion of said fixation element to facilitate insertion of said lead to a point where said fixation element is proximate to said location, said covering being soluble in body fluids and having dissolving characteristics selected so that it dissolves only after being in said body fluids for at least a predetermined time, whereby said covering maintains its structural integrity for at least said predetermined time after being inserted into the patient, said covering having a radiopaque material within at least a portion thereof to provide an x-ray visible target until said covering dissolves but not thereafter, whereby it can be determined when said covering has dissolved by monitoring said lead distal end with x-ray equipment.

2. The implantable lead as described in claim 1, wherein said lead is a pacing lead having a connecting element at its proximal end for connection to a pacemaker, and wherein said covering has radiopaque material mixed within at least a portion thereof.

3. The lead as described in claim 1, wherein said fixation element is a helix.

4. The lead as described in claim 1, wherein the entire said covering is substantially uniformly mixed with said radiopaque material.

5. The lead as described in claim 1, wherein said covering comprises a capsule having an inner cavity filled with said radiopaque material.

6. The lead as described in claim 2, wherein said covering envelops said fixation element.

7. The lead as described in claim 1, wherein said covering comprises mannitol.

8. The lead as described in claim 1, wherein said fixation element comprises tines and said covering holds said tines in a folded position until it dissolves.

9. The lead as described in claim 1, wherein said fixation element is constrained in position by said covering and is free to move after said covering dissolves.

10. A method of implanting a pacing lead in the heart of a patient, said lead having a fixation element at about its distal end and a covering over at least a portion of said fixation element to facilitate insertion of said lead transvenously, said covering being soluble in body fluids and having dissolving characteristics so that it dissolves only after being in said body fluids for at least a predetermined time, said covering being characterized by a containing radiopaque material within at least a portion thereof to render such portion x-ray visible until it dissolves, said method comprising inserting said lead and positioning its distal end proximate to the heart wall of the patient, x-ray monitoring said distal end and determining when said covering has dissolved, and fixing said fixation element to the inside of the patient's heart directly upon determining that said covering has dissolved.

11. The method as described in claim 10, wherein said fixation element is a helix, and said fixing step comprises screwing said helix into said patient's heart tissue.

12. An implantable lead having a distal end and an electrode near said distal end, a proximal end, a flexible length between said distal and proximal ends, and a conductor connecting said proximal end and said electrode, said lead having a fixation element at about said distal end for effecting fixation to body tissue at a selected location in a patient, and a covering over at least a portion of said fixation element to facilitate insertion of said lead to a point where said fixation element is proximate to said location, said covering having an inner cavity filled with a radiopaque material to provide an x-ray visible target until said covering dissolves, whereby it can be determined when said covering has dissolved by monitoring said lead distal end with x-ray equipment.

* * * * *

UNITED STATES PATENT AND TRADEMARK OFFICE
CERTIFICATE OF CORRECTION

PATENT NO. : 5,531,783
DATED : July 2, 1996
INVENTOR(S) : Vincent Giele; Marc Berkhof It is certified that error appears in the above-indentified patent and that said Letters Patent is hereby corrected as shown below:

At col. 3, line 13, "coveting" should read --covering--

Signed and Sealed this

Thirty-first Day of December, 1996

Attest:

BRUCE LEHMAN

*Attesting Officer*  *Commissioner of Patents and Trademarks*